United States Patent
Kim et al.

(10) Patent No.: US 10,898,123 B2
(45) Date of Patent: Jan. 26, 2021

(54) MOTOR FUNCTION ASSESSMENT SYSTEM

(71) Applicant: Daegu Gyeongbuk Institute of Science and Technology, Daegu (KR)

(72) Inventors: Jong Hyun Kim, Daegu (KR); Seunghee Lee, Sejong-si (KR); Sang Hyuk Son, Daegu (KR); Paul Otten, Redmond, WA (US)

(73) Assignee: DAEGU GYEONGBUK INSTITUITE OF SCIENCE AND TECHNOLOGY, Daegu (KR)

( * ) Notice: Subject to any disclaimer, the term of this patent is extended or adjusted under 35 U.S.C. 154(b) by 255 days.

(21) Appl. No.: 15/791,421

(22) Filed: Oct. 24, 2017

(65) Prior Publication Data
US 2018/0125408 A1 May 10, 2018

(30) Foreign Application Priority Data
Nov. 7, 2016 (KR) .......................... 10-2016-0147319

(51) Int. Cl.
| A61B 5/00 | (2006.01) |
| A61B 5/22 | (2006.01) |
| A61B 5/11 | (2006.01) |
| A61B 5/16 | (2006.01) |

(52) U.S. Cl.
CPC .......... *A61B 5/4082* (2013.01); *A61B 5/1125* (2013.01); *A61B 5/16* (2013.01);
(Continued)

(58) Field of Classification Search
CPC ..... A61B 5/4082; A61B 5/225; A61B 5/7267; A61B 5/721; A61B 5/16; A61B 5/1125;
(Continued)

(56) References Cited

U.S. PATENT DOCUMENTS

| 9,460,266 B2 | 10/2016 | Einav et al. | |
| 2012/0021833 A1* | 1/2012 | Boch | G06F 3/011 463/36 |
| 2015/0003687 A1* | 1/2015 | Utsunomiya | G06K 9/00348 382/107 |

FOREIGN PATENT DOCUMENTS

| JP | 2005-348779 | 12/2005 |
| JP | 5458428 | 1/2014 |

(Continued)

OTHER PUBLICATIONS

Kim et al. "The Relationship of Ipsilateral Mirror Movements and Motor Function of the Affected Upper Extremity of Stroke Patients", The Journal of Korean Society of Occupational Therapy, KSOT, 16(1): 89-97, Mar. 10, 2008. English Abstract.

(Continued)

*Primary Examiner* — Michael R Bloch
(74) *Attorney, Agent, or Firm* — Harness, Dickey & Pierce, P.L.C.

(57) ABSTRACT

Disclosed is system for assessing a motor function, the system including a sensor configured to acquire human body exercise information including a joint position, a joint orientation, a grasp state, or a grasp force, a processor configured to extract an exercise feature for analyzing a human body motion time and human body motion information based on the acquired human body exercise information, analyze at least one target motion for assessment based on a set assessment condition using the extracted exercise feature, classify an assessment factor of the at least one target motion for assessment as a success or a failure, and determine a final assessment score of the at least one target motion for assessment based on the classified assessment factor, and a display configured to display the final assessment score.

6 Claims, 15 Drawing Sheets

(52) U.S. Cl.
CPC .............. *A61B 5/225* (2013.01); *A61B 5/721* (2013.01); *A61B 5/7267* (2013.01); *A61B 5/4528* (2013.01)

(58) Field of Classification Search
CPC ..... A61B 5/4528; A61B 5/742; A61B 5/6887; A61B 5/1126
See application file for complete search history.

(56) References Cited

FOREIGN PATENT DOCUMENTS

| | | |
|---|---|---|
| KR | 10-2014-0051554 | 5/2014 |
| KR | 10-2014-0071739 | 6/2014 |
| KR | 10-2016-0002208 | 1/2016 |

OTHER PUBLICATIONS

Lee et al. "Towards Clinically Relevant Automatic Assessment of Upper-Limb Motor Function Impairment", 2016 IEEE-EMBS International Conference on Biomedical and Health Informatics, BHI 2016, LAs Vegas, NV, USA, Feb. 24-27, 2016, p. 148-152, Feb. 24, 2016.

Otten "Automating the Fugl-Meyer Assessment With Supervised Machine Learning", Master's Thesis Submitted to the Faculty of DGIST, Department of Information and Communication Engineering, in Partial Fulfillment of Requirements for the Degree of Master of Science, DGIST Research and Development Program of the Ministry of Science, ICT and Future Planning of Korea, p. 1-38, Nov. 14, 2014.

* cited by examiner

FIG. 3

| Category | Assessment item | | |
|---|---|---|---|
| A. Shoulder /Elbow /Forearm | 2. Volitional movement within synergies<br>  Flexor synergy<br>    Shoulder - Elevation<br>    Shoulder - Abduction<br>    Shoulder – Outward rotation<br>    Elbow - Flexion<br>    Forearm - Supination<br>  Extensor synergy<br>    Shoulder – Adduction/inward rotation<br>    Elbow - Extension<br>    Forearm - Pronation<br>3. Volitional movement mixing synergies<br>  Hand to lumbar spine<br>    Hand – move to lumbar spine<br>  Shoulder flexion 0°– 90°<br>  Elbow 90°- Pronation/supination<br>4. Volitional movement with little or no synergy<br>  Shoulder abduction 0°– 90°<br>  Shoulder flexion 90°– 180°<br>  Elbow 0°- Pronation/supination | | |
| B. Wrist | Repeated dorsiflexion/volar flexion<br>  Elbow 90°- Wrist Flexion/extension<br>Repeated dorsiflexion/volar flexion<br>  Elbow 0°- Wrist Flexion/extension<br>Circumduction<br>  Circumduction | | |
| C. Hand | Mass flexion<br>Mass extension<br>Grasp A<br>Grasp B<br>Grasp C<br>Grasp D<br>Grasp E | | |
| D. Coordination /Speed | Dysmetria<br>Speed | | |

FIG. 12

| | Feature | Threshold | Example of experimental data Mean/STD | Logical expression |
|---|---|---|---|---|
| A | Elbow flexion angle during onset phase (Mean/STD) | >120° | 163.4/0.5 | 1 |
| B | Shoulder abduction angle during onset phase (Mean/STD) | >60° | 84.4/1.1 | 1 |
| C | Shoulder flexion angle during onset phase (Mean) | <30° | 10.9 | 1 |
| D | Shoulder flexion angle during motion phase (ROM) | >30° | 52.1 | 1 |
| E | Shoulder flexion angle during motion phase (ROM) | >60° | 52.1 | 0 |
| F | Elbow flexion angle during motion phase (Mean/STD) | >120° | 156.9/3.9 | 1 |
| G | Shoulder abduction angle during motion phase (Mean/STD) | >60° | 82.3/15.3 | 0 |
| H | Pronation angle during motion phase (Mean/STD) | >-30°, <30° | -24.4/13.2 | 0 |

FIG. 13

| A | B | C | D | E | F | G | H | FMA score |
|---|---|---|---|---|---|---|---|---|
| 0 | 0 | 0 | 0 | 0 | 0 | 0 | 0 | 0 |
| 0 | 0 | 0 | 0 | 0 | 0 | 0 | 1 | 0 |
| 0 | 0 | 0 | 0 | 0 | 0 | 1 | 0 | 0 |
| 0 | 0 | 0 | 0 | 0 | 0 | 1 | 1 | 0 |
| ..... | | | | | | | | |
| 1 | 1 | 1 | 1 | 0 | 0 | 0 | 0 | 1 |
| 1 | 1 | 1 | 1 | 0 | 0 | 0 | 1 | 1 |
| 1 | 1 | 1 | 1 | 0 | 0 | 1 | 0 | 1 |
| 1 | 1 | 1 | 1 | 0 | 0 | 1 | 1 | 1 |
| 1 | 1 | 1 | 1 | 0 | 1 | 0 | 0 | 1 |
| ..... | | | | | | | | |
| 1 | 1 | 1 | 1 | 1 | 1 | 1 | 1 | 2 |

MOTOR FUNCTION ASSESSMENT SYSTEM

RELATED APPLICATION

This application claims the benefit of priority of Korean Patent Application No. 10-2016-0147319 filed on Nov. 7, 2016, the contents of which are incorporated herein by reference in their entirety.

FIELD AND BACKGROUND OF THE INVENTION

1. Field

One or more example embodiments relate to a motor function assessment system.

2. Description of Related Art

A Fugl-Meyer Assessment (FMA) may be a method of assessing a sensorimotor impairment of a patient with a brain disease. The FMA may have a sequential score system for assessing the sensorimotor impairment. In the FMA, a score of 0 may be assigned as an assessment score of a predetermined motion when the patient does not perform the motion, a score of 1 may be assigned as the assessment score of the motion when the patient performs the motion partially, and a score of 2 may be assigned as the assessment score of the motion when the patient fully performs the motion.

For example, Korean Patent Application No. 10-2014-0071739 discloses Method and apparatus for evaluating of rehabilitation using EMG signal of upper limb.

SUMMARY OF THE INVENTION

An aspect provides a motor function assessment system that calculates a final assessment score of a target motion for assessment with increased accuracy and confidence level by objectifying an FMA which have been conducted subjectively by a clinician in general.

Another aspect provides a motor function assessment system that automatically calculates a final assessment score of a target motion for assessment based on human body motion information newly inputted through machine learning by accumulating result data including the final assessment score of the target motion for assessment.

Still another aspect provides a motor function assessment system that uses a contactless sensor which is also applicable to a user with a brain disease.

Yet another aspect provides a motor function assessment system that minimizes a number of sensors configured to sense human body exercise information.

Further aspect provides a motor function assessment system that determines a final assessment score of a target motion for assessment independently of a large amount of patient experiment data and accurately assessed patient data.

According to an aspect, there is provided a system for assessing a motor function, the system including a sensor configured to acquire human body exercise information including a joint position, a joint orientation, a grasp state, or a grasp force, a processor configured to extract an exercise feature for analyzing a human body motion time and human body motion information based on the acquired human body exercise information, analyze at least one target motion for assessment based on a set assessment condition using the extracted exercise feature, classify an assessment factor of the at least one target motion for assessment as a success or a failure, and determine a final assessment score of the at least one target motion for assessment based on the classified assessment factor, and a display configured to display the final assessment score.

The sensor may include a motion recognition sensor configured to sense the joint position, the joint orientation, or the grasp state and a pressure sensor configured to sense the grasp force.

The processor may be configured to extract the joint orientation of the human body exercise information in a form of quaternion, convert a bone orientation in the form of quaternion into Euler angles to analyze the at least one target motion for assessment, and analyze the at least one target motion for assessment by comparing the grasp state to set confidence level information.

The processor may be configured to change the determined final assessment score based on an input of a user.

The system may further include a storage configured to store the acquired human body exercise information and the determined final assessment score as result data, wherein the processor may be configured to train a neural network based on the result data and determine a final assessment score of a target motion for assessment based on human body exercise information input from a user through the neural network.

According to another aspect, there is provided a system for assessing a motor function, the system including a processor configured to determine a final assessment score of a target motion for assessment based on human body exercise information including a joint position and a joint orientation in a human body, wherein the target motion for assessment includes a first assessment motion of a first joint of the human body moving in a set direction from a first virtual line of the human body and a second assessment motion of a second joint of the human body moving in a set range from a second virtual line of the human body, and wherein the processor is configured to determine the final assessment score of the target motion for assessment based on a set condition using an assessment factor of the first assessment motion and an assessment factor of the second assessment motion.

The processor may be configured to determine an assessment score of the first assessment motion by a first assessment factor and a second assessment factor, assign a score of 0 to each of the first assessment factor and the second assessment factor when the first joint is at an angle within a first angle range from the first virtual line, assign a score of 1 to the first assessment factor and a score of 0 to the second assessment factor when the first joint is at an angle within a second angle range from the first virtual line, and assign a score of 1 to each of the first assessment factor and the second assessment factor when the first joint is at an angle within a third angle range from the first virtual line.

The processor may be configured to extract, from a normal distribution of angular displacements of the first joint in a period of time in which the first assessment motion is performed, standard deviations of angular displacements of the first joint in a window of a set size on a time-by-time basis, determine a result value obtained by multiplying, by a set proportion value, a maximum standard deviation having a greatest value among the extracted standard deviations, and set, to be a motion phase, a period of time from a point in time of a minimum value among points in time corresponding to standard deviations of which the result value is the same among the extracted standard deviations to a point in time of a maximum value among the points in time.

The processor may be configured to determine an assessment score of the second assessment motion by a third assessment factor, extract a standard deviation of angular displacements of the second joint, assign a score of 1 to the third assessment factor when the second joint is at an angle within a fourth angle range from the second virtual line and the standard deviation of the angular displacements of the second joint is less than the result value, and assign a score of 0 to the third assessment factor when the second joint is at an angle within a fifth angle range from the second virtual line or the standard deviation of the angular displacements of the second joint is greater than or equal to the standard deviation of the angular displacements of the first joint.

The processor may be configured to set, to be an onset phase, a period of time from a point in time earlier than the point in time of the minimum value by a set amount of time to a point in time later than the point in time of the minimum value by the amount of time.

The processor may be configured to discard human body exercise information acquired in a period of time other than the motion phase.

The human body exercise information may include a grasp force of the human body and the target motion for assessment may include a third assessment motion of a hand of the human body opening and closing, and the processor is configured to determine an assessment score of the third assessment motion based on a fourth assessment factor, assign a score of 0 to the fourth assessment factor when the grasp force is not sensed or the grasp force is less than a set force, and assign a score of 1 to the fourth assessment factor when the grasp force is greater than or equal to the set force.

The processor may be configured to determine the final assessment score using an equation as follows:
if $$A*B*C*E*F*G*H=1, FMA=2,$$

Else $$FAS=A*B*C*E*F'+A*B*C*E*F+A*B*C*D*F+A*B*C*D*F',$$

where A, B, and C denote assessment factors of the second assessment motion in an onset phase, D and E denote assessment factors of the first assessment motion in a motion phase, F, G, and H denote assessment factors of the second assessment motion in the motion phase, and FAS denotes the final assessment score.

Additional aspects of example embodiments will be set forth in part in the description which follows and, in part, will be apparent from the description, or may be learned by practice of the disclosure.

BRIEF DESCRIPTION OF THE SEVERAL VIEWS OF THE DRAWINGS

These and/or other aspects, features, and advantages of the invention will become apparent and more readily appreciated from the following description of example embodiments, taken in conjunction with the accompanying drawings of which:

FIG. 3 is a diagram illustrating a list of target motions for assessment according to an example embodiment;

FIG. 12 is a diagram illustrating an assessment condition for assigning a score to an assessment factor of a target motion of assessment in a processor according to an example embodiment;

FIG. 13 is a diagram illustrating a table used for determining a final assessment score in a processor according to an example embodiment;

DESCRIPTION OF SPECIFIC EMBODIMENTS OF THE INVENTION

Figure 1:
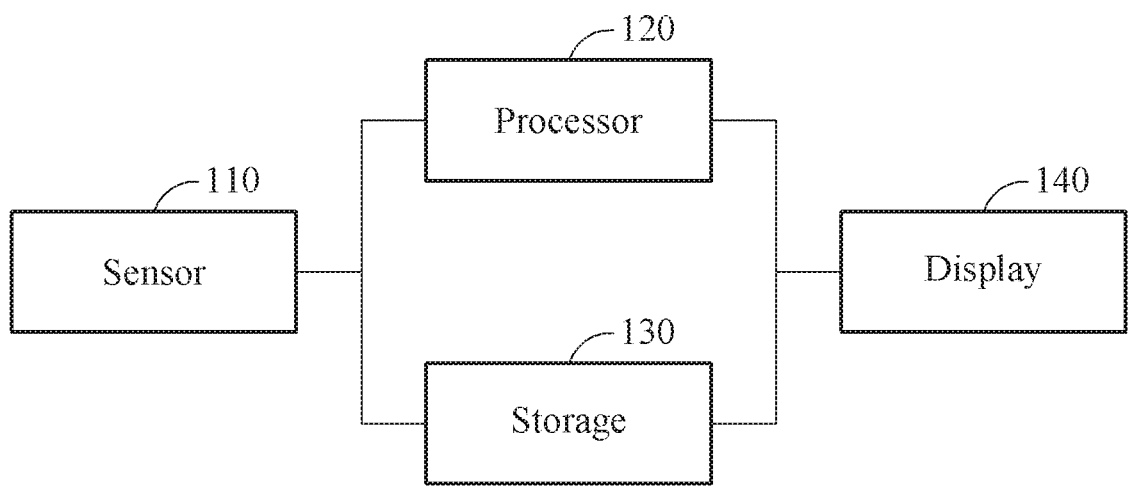
FIG. 1 is a block diagram illustrating a motor function assessment system according to an example embodiment.

Hereinafter, example embodiments will be described in detail with reference to the accompanying drawings. It should be understood, however, that there is no intent to limit this disclosure to the particular example embodiments disclosed. On the contrary, example embodiments are to cover all modifications, equivalents, and alternatives falling within the scope of the example embodiments.

Although terms such as "first," "second," and "third" may be used herein to describe various members, components, regions, layers, or sections, these members, components, regions, layers, or sections are not to be limited by these terms. Throughout the specification, when an element, such as a layer, region, or substrate, is described as being "on," "connected to," or "coupled to" another element, it may be directly "on," "connected to," or "coupled to" the other element, or there may be one or more other elements intervening therebetween.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

FIG. 1 is a block diagram illustrating a motor function assessment system according to an example embodiment and FIG. 3 is a diagram illustrating a list of target motions for assessment according to an example embodiment.

Referring to FIGS. 1 and 3, a motor function assessment system 1 may be a system for analyzing a motion characteristic of a person with a brain disease. The motor function assessment system 1 may calculate a final assessment score of at least one target motion for assessment based on a set assessment condition. In this disclosure, the final assessment score may also be referred to as a Fugl-Meyer assessment (FMA) score. The motor function assessment system 1 is applicable not only to the person with the brain disease, but also to various fields for analyzing human motion characteristics.

In this disclosure, a target motion for assessment may be a motion corresponding to a target for assessing a motor function of a human body. For example, the motor function assessment system 1 may assess a target motion for assessment such as a motion to be performed at a shoulder, an elbow, and/or, a forearm and a motion performed at a wrist and a hand.

The motor function assessment system 1 may include a sensor 110, a processor 120, a storage 130, and a display 140.

The sensor 110 may acquire exercise information of a human body including a joint position, a joint orientation, a grasp state, or a grasp force. The sensor 110 may acquire the exercise information in real time.

The processor 120 may extract an exercise feature for analyzing motion information and a motion time of the human body from the exercise information acquired by the sensor 110. The motion information may be information on a motion of a human body such as an arm, a shoulder, a wrist, and a hand flexed, extended, rotating, or moving in a predetermined direction. The motion time may be a time in which the motion of the human body is performed. Also, the motion may be a target motion for assessment as further discussed below.

The processor 120 may analyze at least one target motion for assessment based on a set assessment condition using the extracted exercise feature and assign a score to at least one assessment factor configuring the target motion for assessment.

A number of assessment factors may be determined based on, for example, a motion range of the target motion for assessment and the motion time of the target motion for assessment. For example, when a motion range of a target motion for assessment is divided into three phases, the number of assessment factors configuring the target motion for assessment may be determined as 2. In this example, a score to be assigned to an assessment factor may vary based on a phase to which the motion range of the target motion for assessment belongs.

The processor 120 may classify the at least one assessment factor configuring the target motion for assessment as a success or a failure. In this disclosure, the success or the failure may also be represented as true or fail and a score of 1 or a score of 0. The processor 120 may analyze the target motion for assessment based on Boolean algebra.

The processor 120 may classify the at least one assessment factor configuring the target motion for assessment as a success or a failure. In this disclosure, the success or the failure may also be represented as true or false and a score of 1 or a score of 0. The processor 120 may analyze the target motion for assessment based on Boolean algebra.

The storage 130 may store the exercise information acquired by the sensor 110 and the final assessment score determined by the processor 120 as result data. The result data may be provided in a form suitable for training the neural network included in the processor 120.

The display 140 may display the final assessment score. The display 140 may include, for example, a cathode ray tube (CRT) display, a liquid crystal display (LCD), a plasma display panel (PDP), an organic light-emitting diode (OLED) display, a field-emission display (FED), a light-emitting diode (LED) display, a vacuum fluorescent display (VFD), a digital light processing (DLP) display, a primary flight display (PFD), a three-dimensional (3D) display, a transparent display, and other display devices known by those skilled in the art.

Figure 2:
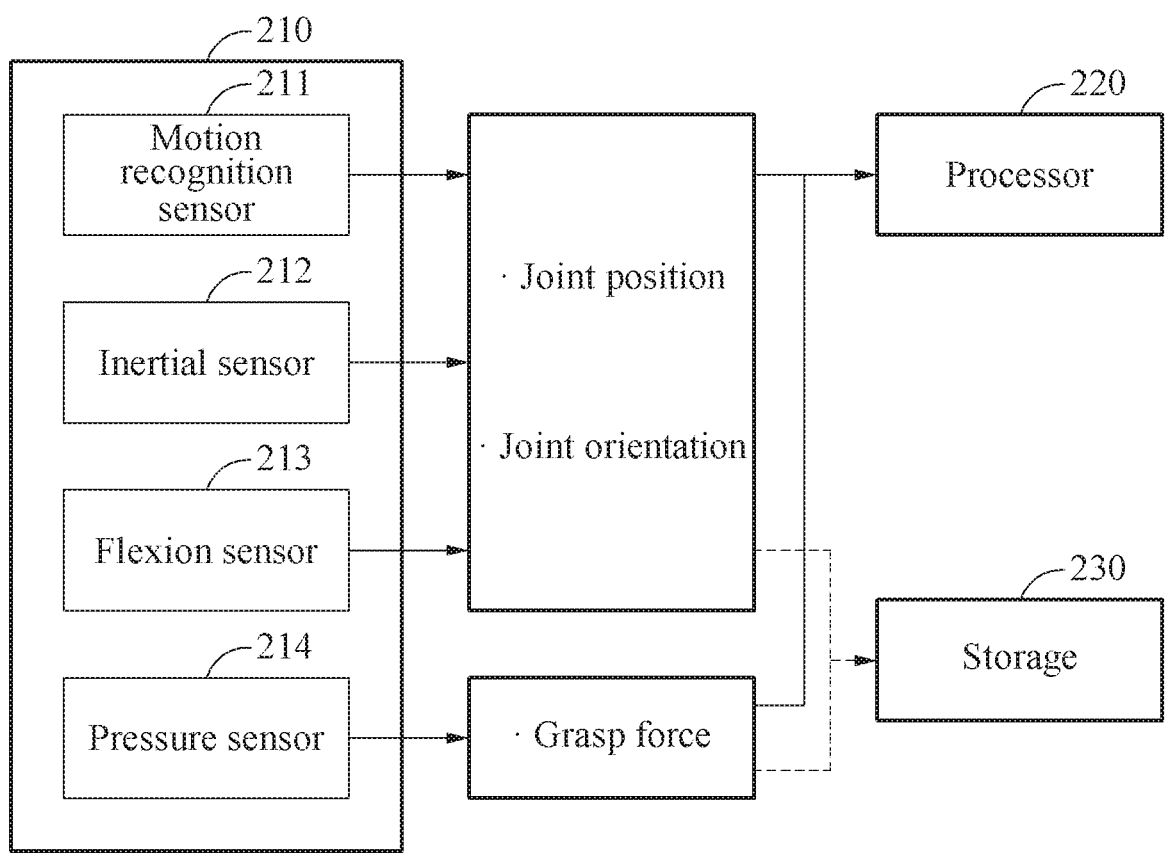
FIG. 2 is a block diagram illustrating a connection of a sensor, a processor, and a storage according to an example embodiment.

FIG. 2 is a block diagram illustrating a connection of a sensor, a processor, and a storage according to an example embodiment.

Referring to FIG. 2, a motor function assessment system 2 may include a sensor 210, a processor 220, a storage 230, and a display (now shown) connected to the processor 220 and the storage 230.

The sensor 210 may include at least one of a motion recognition sensor 211, an inertial sensor 212, a flexion sensor 213, and a pressure sensor 214.

The motion recognition sensor 211 may sense a joint position, a joint orientation, and a grasp state of a human body. The inertial sensor 212 may sense the joint position and the joint orientation. The flexion sensor 213 may sense the grasp state. For example, the flexion sensor 213 may be provided in a form of a glove worn on a hand. In this example, the flexion sensor 213 may include a wire extending from a palm part to a finger part. When the hand opens and closes, a length of the wire may increase and decrease whereby the grasp state of the hand is sensed. The pressure sensor 214 may sense a grasp force of the human body. The pressure sensor 214 may be provided on a member of a form to be grasped with the hand, for example, a cylindrical form. Based on a degree to which the member is grasped with the hand, the grasp force may be sensed by the pressure sensor 214.

The exercise information including the grasp force sensed by the pressure sensor 214 or the joint position and the joint orientation sensed by the motion recognition sensor 211, the inertial sensor 212, and the flexion sensor 213 may be transferred to the processor 220 and the storage 230.

The sensor 210 may include four sensors, for example, the motion recognition sensor 211, the inertial sensor 212, the flexion sensor 213, and the pressure sensor 214. In this example, the motion recognition sensor 211 may sense a joint position and a joint orientation of a human body as viewed from a global viewpoint. Also, the inertial sensor 212 and the flexion sensor 213 may be formed integrally. For example, the inertial sensor 212 may be attached to the flexion sensor 213 that is provided in the form of the glove. In this example, the inertial sensor 212 may sense the joint position and the joint orientation of the hand while the flexion sensor 213 senses the grasp state of the hand.

The sensor 210 may include two sensors, for example, the motion recognition sensor 211 and the pressure sensor 214. In this example, the motion recognition sensor 211 may sense a joint position and a joint orientation of a joint of a human body (e.g. a hand joint) as viewed from a local viewpoint in addition to the joint position and the joint orientation as viewed from the global viewpoint. The inertial sensor 212 and the flexion sensor 213 may not be used. Through this, it is possible to solve a difficulty of wearing or attaching the inertial sensor 212 and the flexion sensor 213 to a human body, which may occur due to muscle synergy patterns caused by a muscle contracture of a patient suffering from a brain disease such as a chronic stroke.

Figure 4:
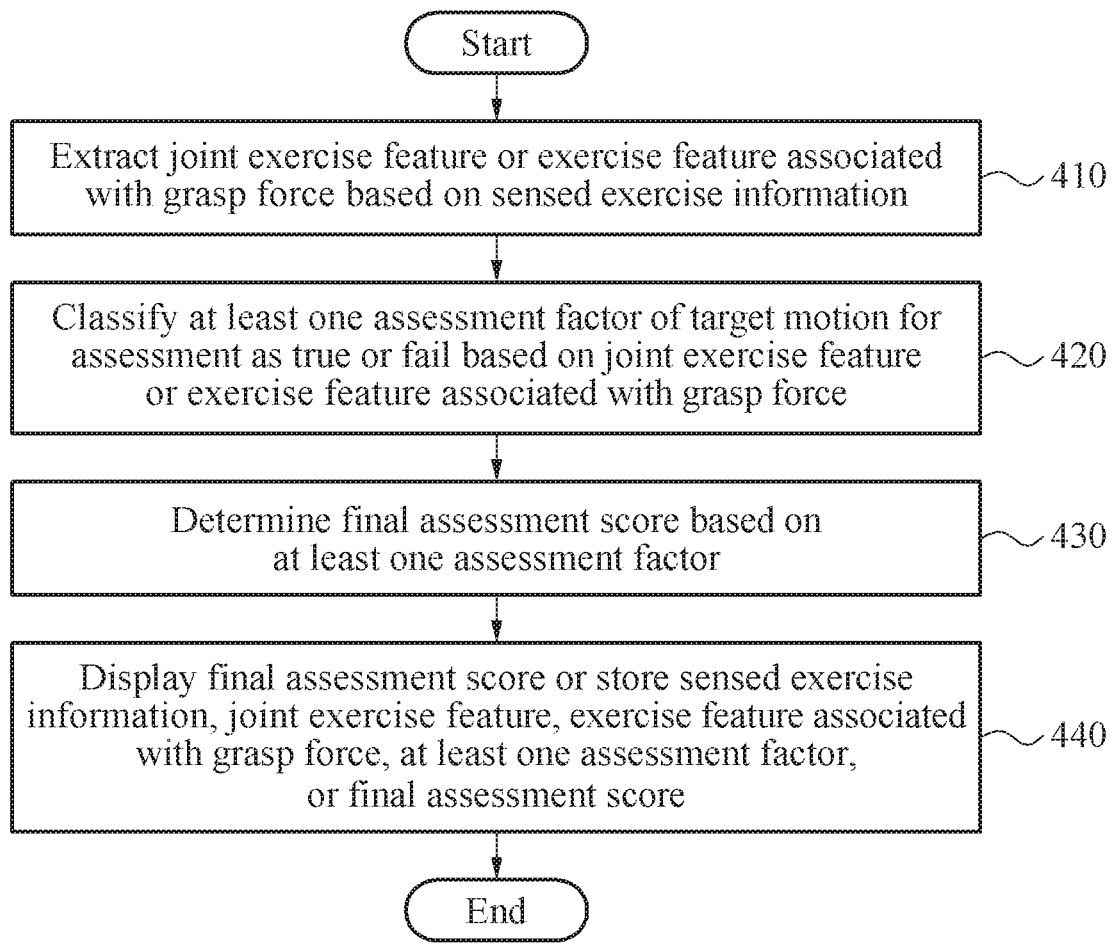
FIG. 4 is a flowchart illustrating a scheme of calculating a Fugl-Meyer assessment (FMA) score in a processor according to an example embodiment.

FIG. 4 is a flowchart illustrating a scheme of calculating an FMA score in a processor according to an example embodiment.

Referring to FIG. 4, in operation 410, a processor may extract a joint exercise feature or an exercise feature associated with the grasp force based on sensed exercise information. Here, the joint exercise feature or the exercise feature associated with the grasp force may be used for analyzing motion information and a motion time of a target motion for assessment performed by a human body and may be information associated with a joint position, a joint orientation, a grasp state or the grasp force, which is provided in a form to be processed by the processor. For example, the joint position and the joint orientation may be extracted in a form of quaternion.

In operation 420, the processor may classify at least one assessment factor of the target motion for assessment as true or false based on the joint exercise feature or the exercise feature associated with the grasp force. For example, the processor may assign a score to the at least one assessment factor of the target motion for assessment based on a Boolean algebra.

In operation 430, the processor may determine a final assessment score, for example, an FMA score based on the at least one assessment factor of the target motion for assessment.

In operation 440, the processor may display the determined final assessment score, or store the sensed exercise information, the joint exercise feature, the exercise feature associated with the grasp force, the at least one assessment factor, or the final assessment score.

Since a large amount of exercise information is not required for learning of the processor in the scheme of calculating the final assessment using the processor, an accurate final assessment score may be obtained based on a relatively small amount of exercise information and thus, the scheme is easily applicable to a clinical field. Also, since the scheme does not depend on the machine learning, only an incorrectly learned logical structure may be selectively removed and an algorithm of the processor may be easily corrected in comparison to a scheme of calculating a final assessment score based on the machine learning, the scheme in which it is difficult to correct an algorithm of the processor trained based on incorrect exercise information.

Figure 5:
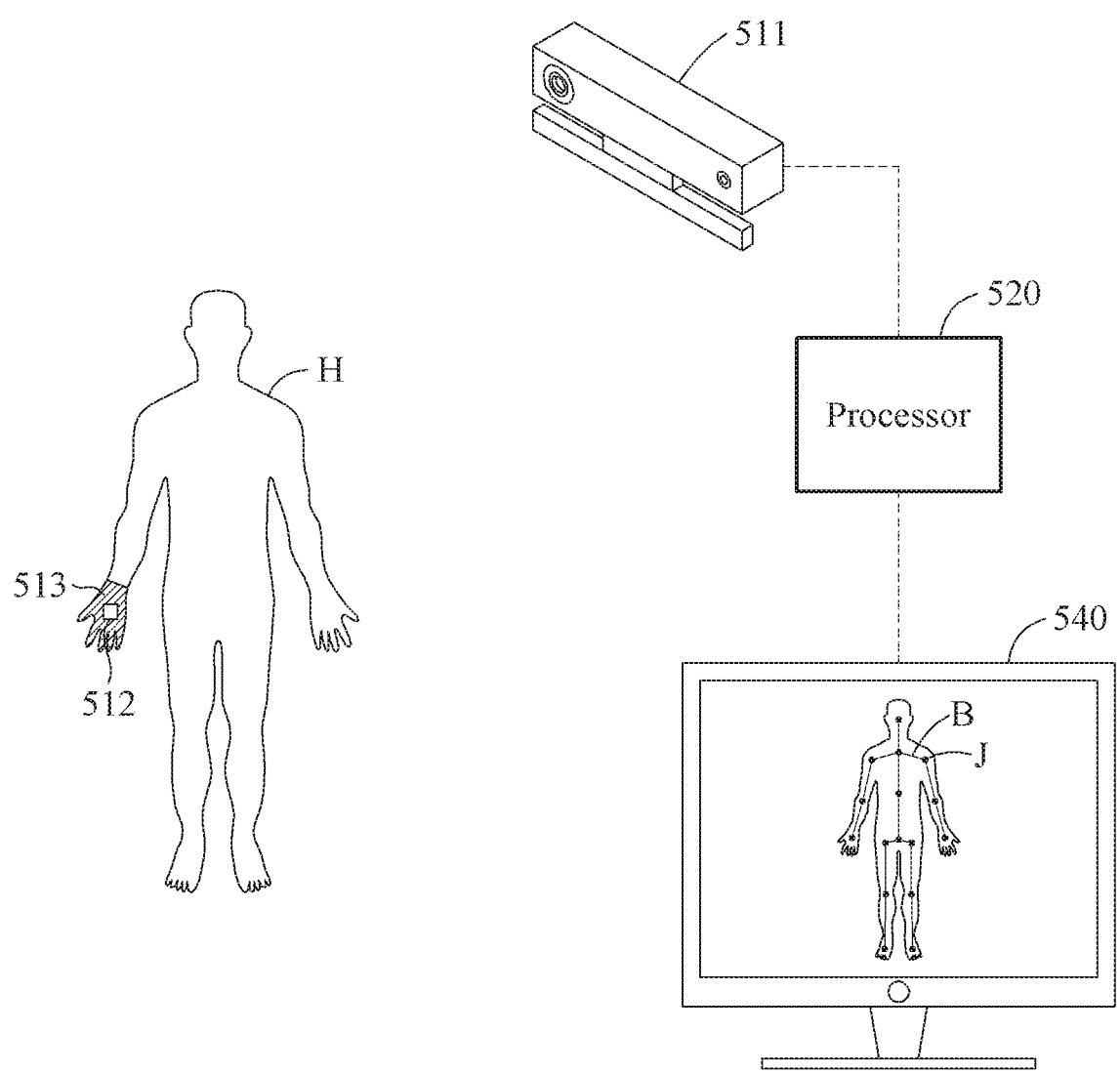
FIG. 5 is a diagram illustrating an example of a motor function assessment system according to an example embodiment.

FIG. 5 is a diagram illustrating an example of a motor function assessment system according to an example embodiment.

Referring to FIG. 5, a motor function assessment system 5 may include a sensor including at least one of a motion recognition sensor 511, an inertial sensor 512, and a flexion sensor 513, a processor 520, a storage (not shown), and a display 540.

The motion recognition sensor 511 may be disposed to face a human body to sense a position of a joint of the human body and an orientation of a bone positioned adjacent to the joint. In FIG. 5, H denotes a human body, J denotes a joint, and B denotes a bone. The inertial sensor 512 may sense a position and an orientation of a joint configuring a hand of the human body. The flexion sensor 513 may sense a grasp state of the hand. As described above, the inertial sensor 512 and the flexion sensor 513 may be formed integrally.

For example, the inertial sensor 512 and the flexion sensor 513 may not be provided. In this example, the motion recognition sensor 511 may sense the position and the orientation of the joint configuring the hand and the grasp state of the hand.

Using the aforementioned structure, even when the inertial sensor 512 (e.g. inertial measurement unit, IMU) and the flexion sensor 513 in a form of glove (e.g. cyberglove) are not used, an angle of a folded finger and a pronation or a supination of a forearm may be acquired. Through this, a number of used sensors may be significantly reduced, which may also reduce costs and a sensor attachment time and increase applicability to a clinical field. In addition, as described above, it is possible to assess a target motion for assessment performed by a user with a brain disease. Also, since sensors are indirectly attached to a human body, inconvenience or uncomfortableness caused by a sensor may be prevented.

Figure 6:
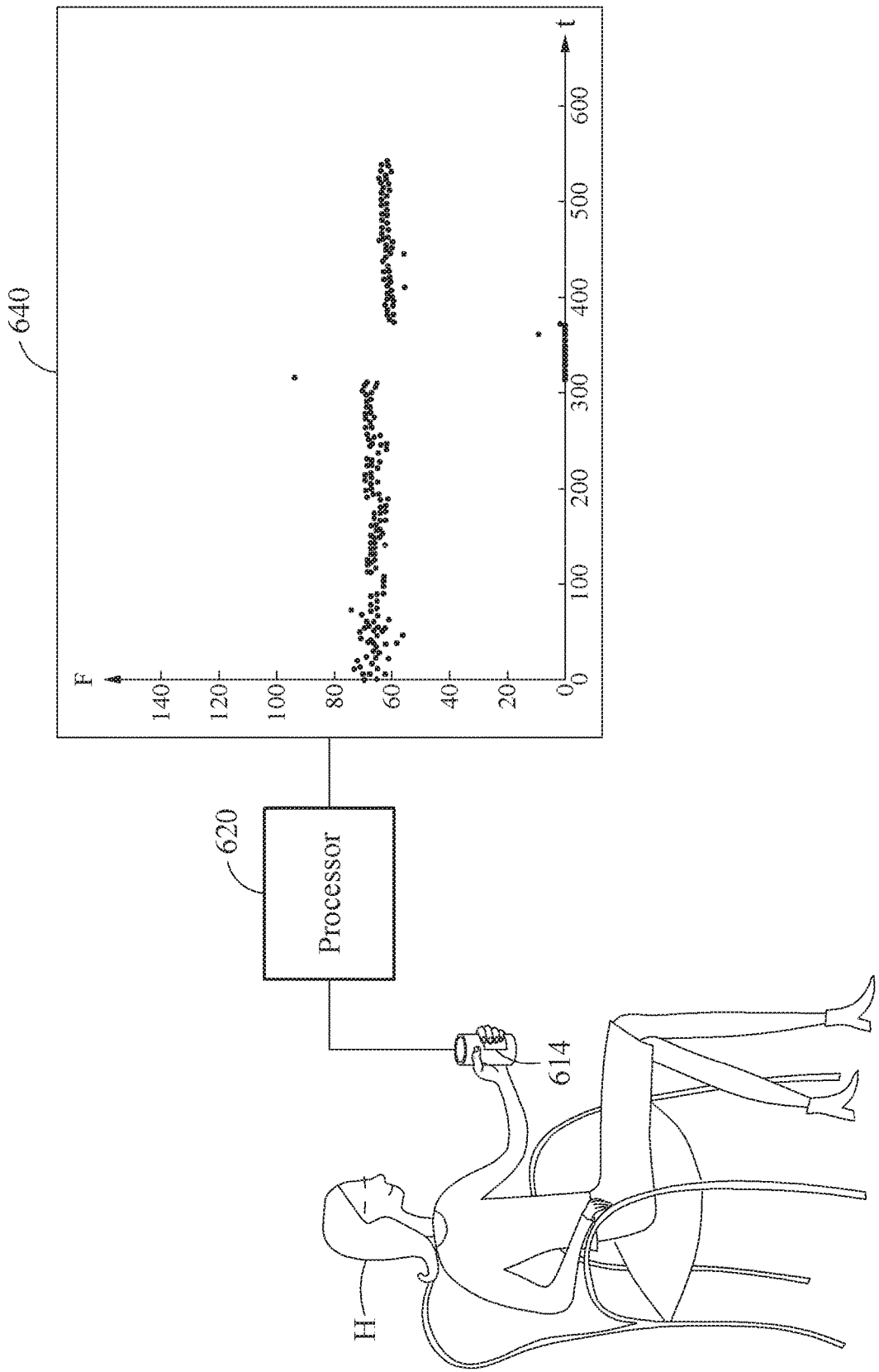
FIG. 6 is a diagram illustrating another example of a motor function assessment system according to an example embodiment.

FIG. 6 is a diagram illustrating another example of a motor function assessment system according to an example embodiment.

Referring to FIG. 6, a motor function assessment system 6 may include a sensor including a pressure sensor 614, a processor 620, a storage (not shown), and a display 640.

The pressure sensor 614 may be provided in a form suitable to be grasped by a hand of a human body H. When the pressure sensor 614 is grasped by the hand, the pressure sensor 614 may sense a grasp force of the human body. The sensed grasp force may be displayed on the display 640 as a graph illustrating a force F and a grasp time t.

Figure 7:
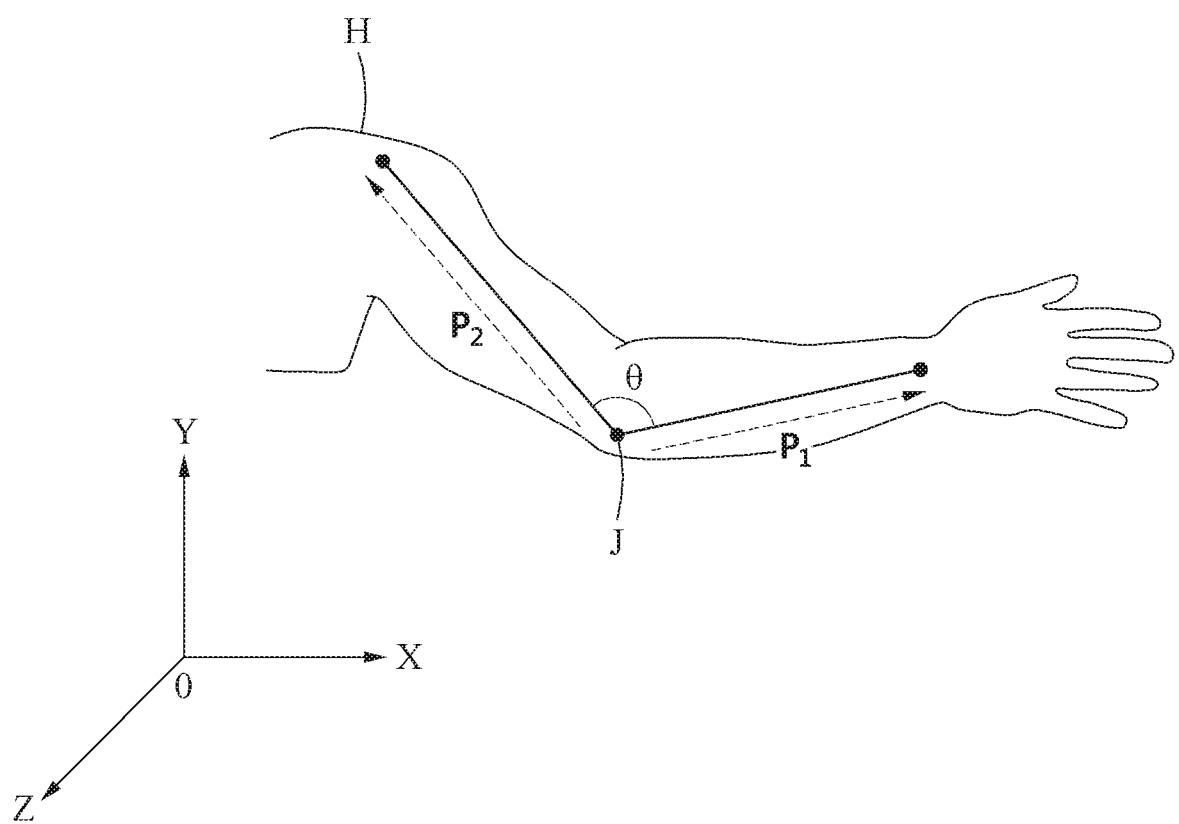
FIG. 7 is a diagram illustrating an example of extracting data using a processor according to an example embodiment.
Figure 8:
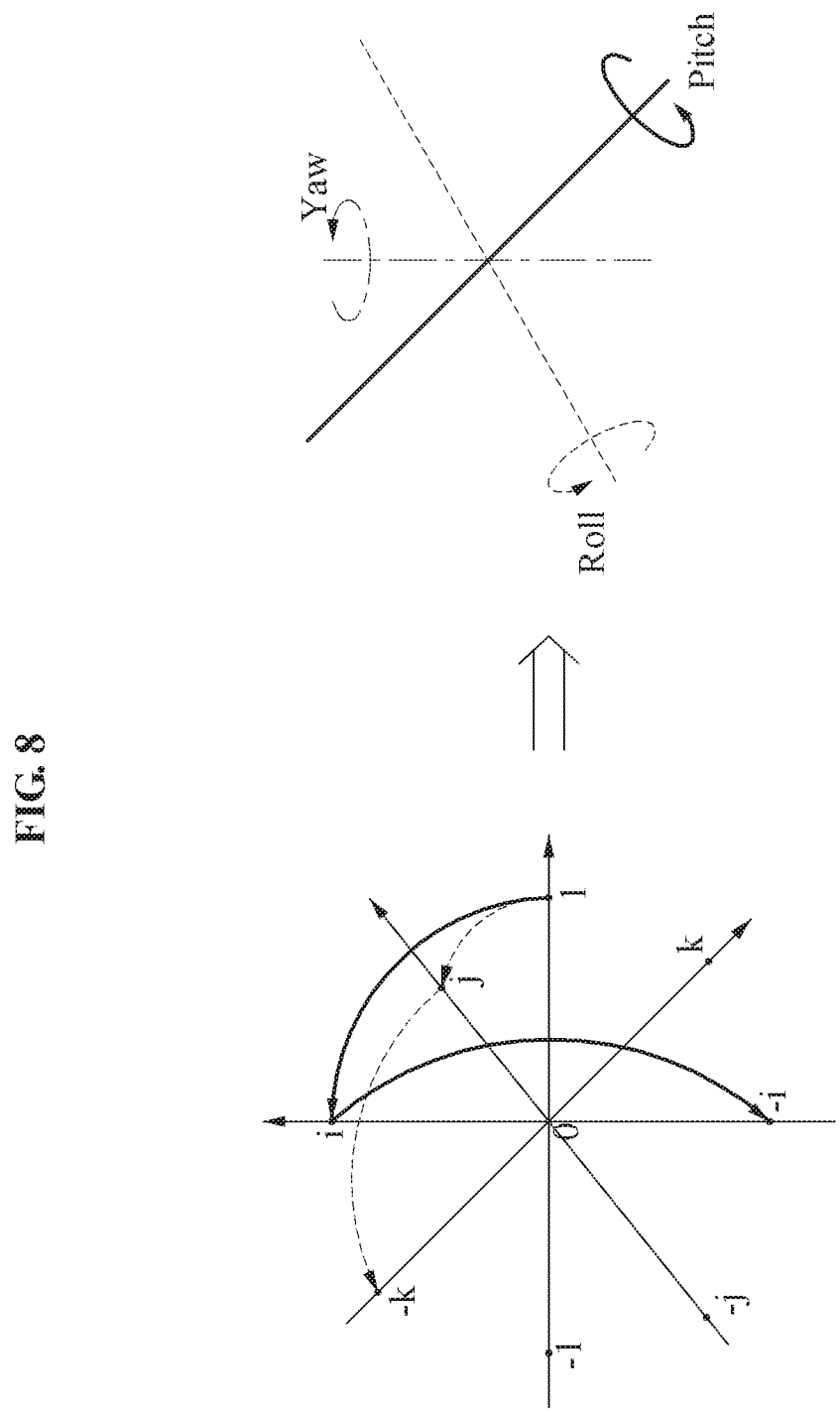
FIG. 8 is a diagram illustrating another example of extracting data using a processor according to an example embodiment.

FIG. 7 is a diagram illustrating an example of extracting data using a processor according to an example embodiment and FIG. 8 is a diagram illustrating another example of extracting data using a processor according to an example embodiment.

Referring to FIGS. 7 and 8, a processor may extract a position of a joint J of a human body, orientations $P_1$ and $P_2$ of bones positioned adjacent to the joint J, and an angle θ between the bones as joint exercise features.

The processor may extract an orientation of a bone positioned adjacent to the joint J from sensed exercise information of the human body to be in a form of quaternion. The quaternion may be a number represented as, for example, "a+bi+ck+dk" using three imaginary units i, j, and k. Here, a, b, c, and d are real numbers. The processor may extract the orientation of the bone in a form of quaternion, for example, "x-y-z-w" and convert the extracted orientation of the bone into roll, pitch, and yaw corresponding to Euler angles. The processor may analyze a target motion for assessment using a converted roll value as rotation value of the bone. For example, when a target motion for assessment of a hand opening and closing is performed, the processor may extract an orientation of a bone configuring the hand in the form of quaternion and convert the extracted orientation into the Euler angles. Among the Euler angles, the processor may use a roll value as rotation information of the hand to analyze pronation and supination motions of a forearm.

The processor may compare a sensed grasp state of the hand to confidence level information to analyze a target motion for assessment. The confidence level information may indicate a number of the same results obtained in an error range when an experiment is repetitively performed a number of times. The processor may accumulate data associated with the grasp state and set the data to be the confidence level information. When the target motion for assessment of the hand opening and closing is performed again, the processor may compare the set confidence level information to a grasp state of the re-performed target motion for assessment to analyze the target motion for assessment.

Figure 9:
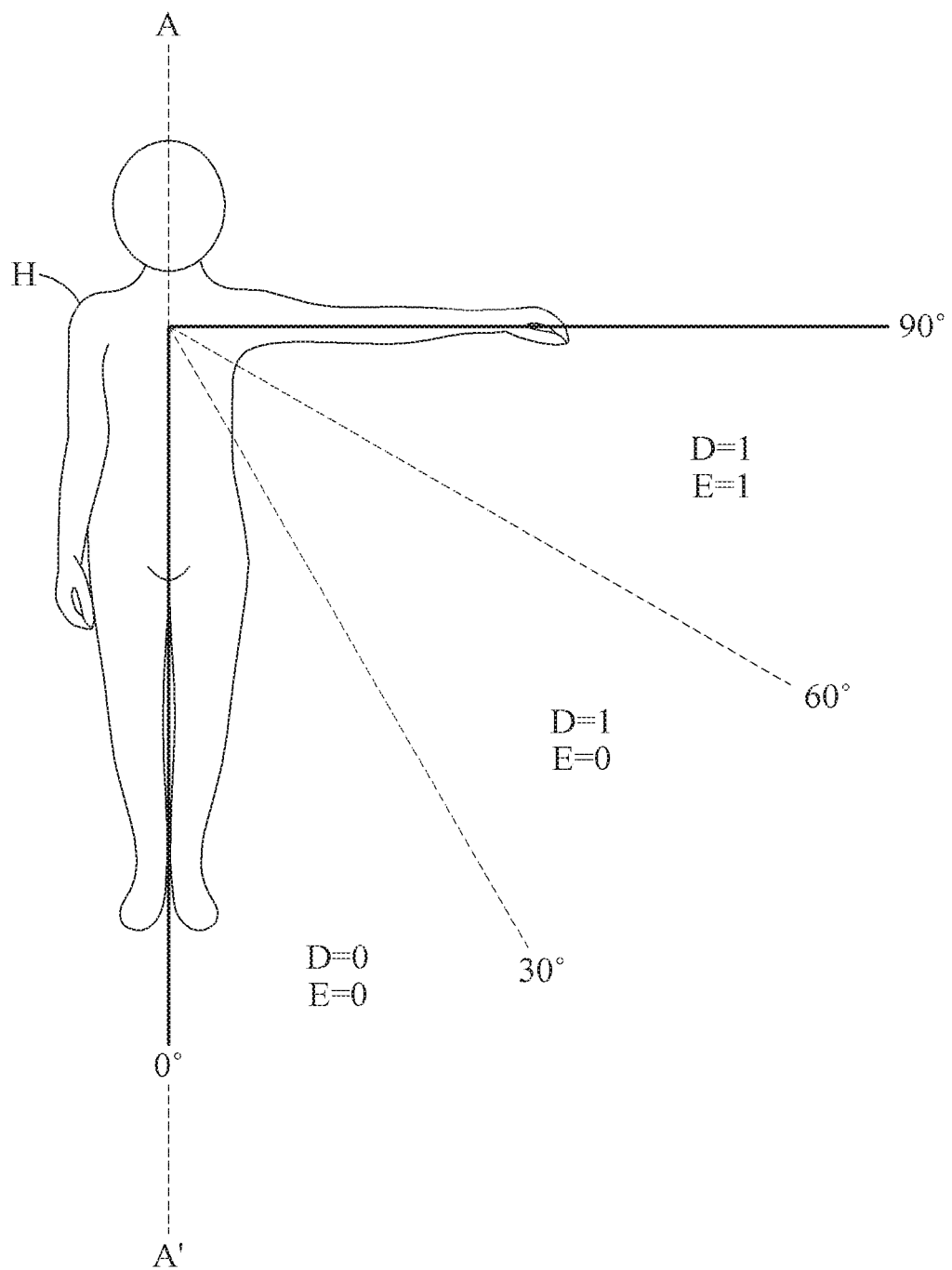
FIG. 9 is a diagram illustrating an example of assigning a score to an assessment factor of a target motion for assessment using a processor according to an example embodiment.
Figure 10:
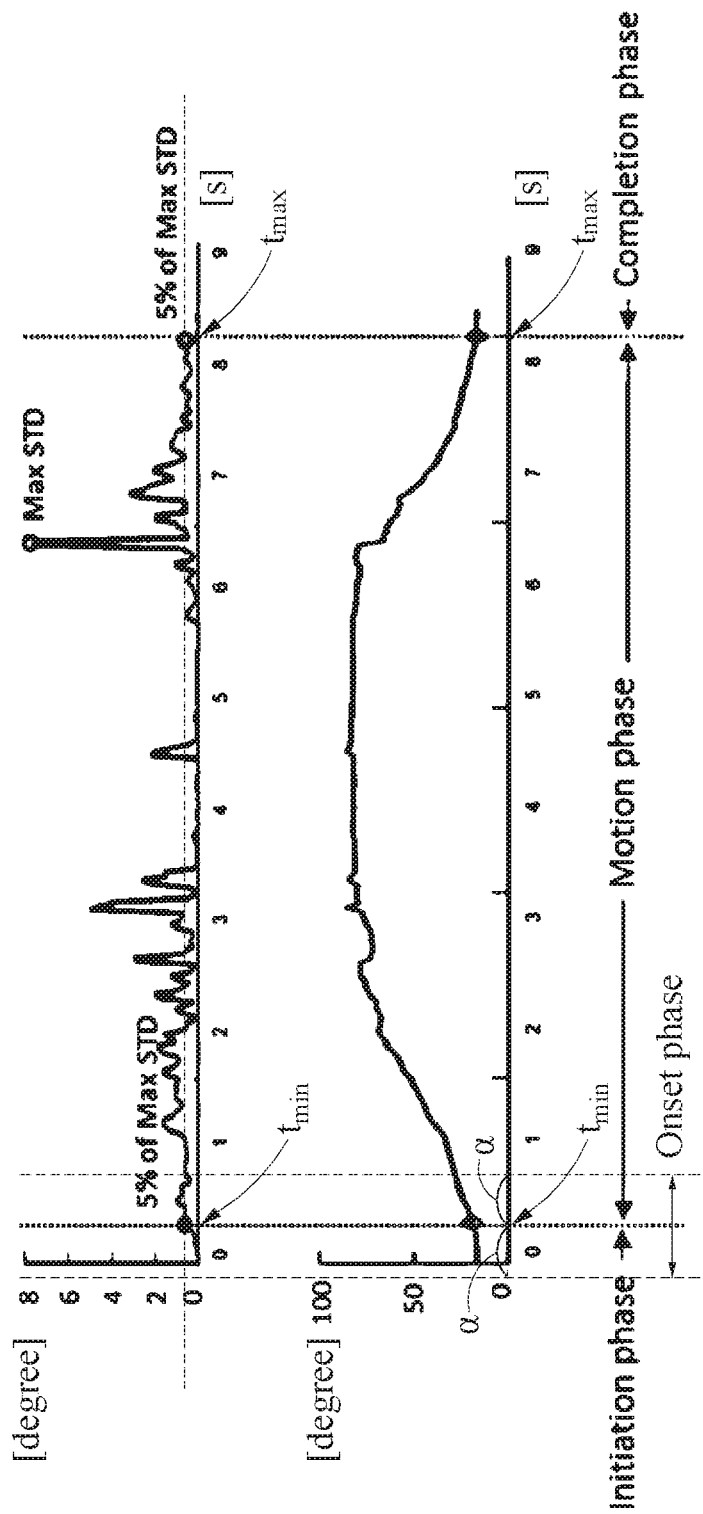
FIG. 10 is a graph illustrating a scheme of determining a motion phase of a target motion of assessment using a processor in a period of time in which the target motion for assessment is performed according to an example embodiment.
Figure 11:
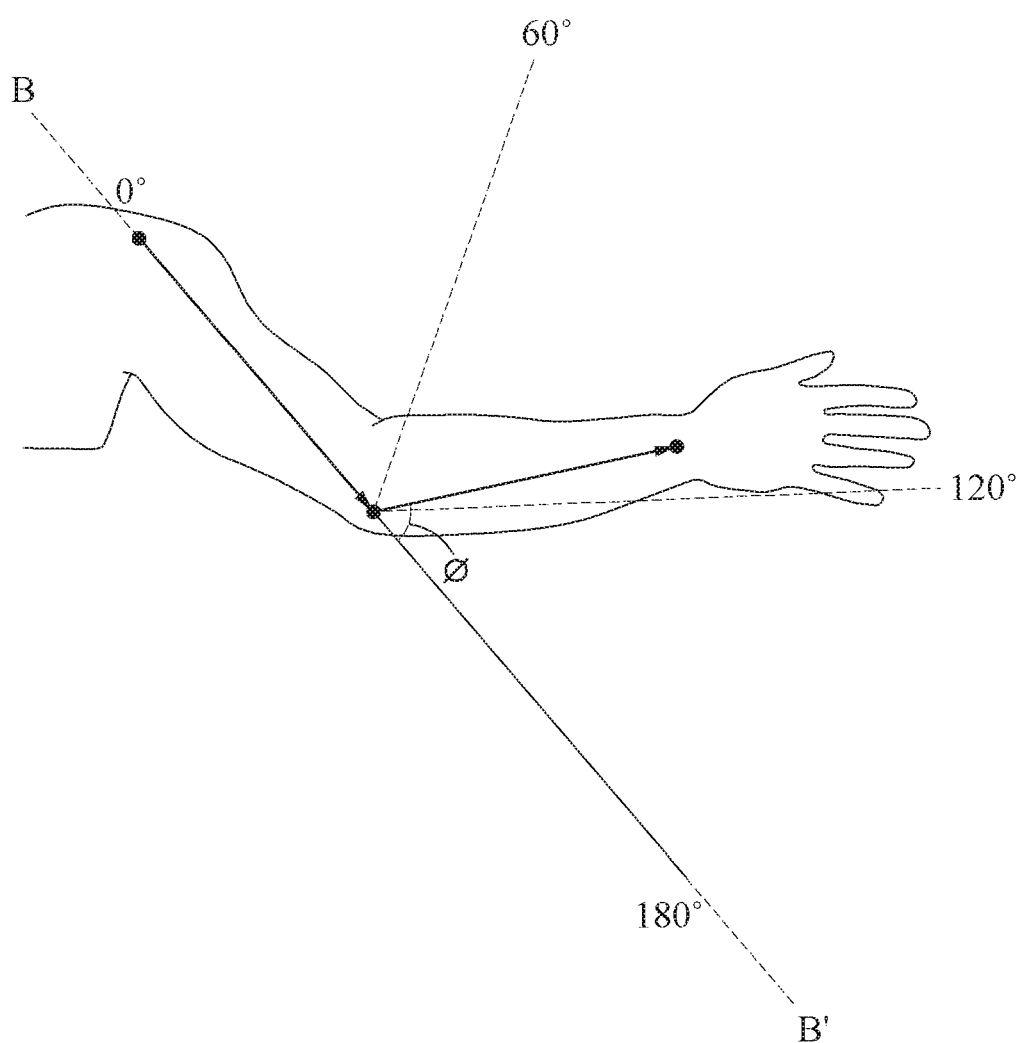
FIG. 11 is a diagram illustrating an example of assigning a score to an assessment factor of a target motion for assessment in a processor according to an example embodiment.

FIG. 9 is a diagram illustrating an example of assigning a score to an assessment factor of a target motion for assessment using a processor according to an example embodiment, FIG. 10 is a graph illustrating a scheme of determining a motion phase of a target motion of assessment using a processor in a period of time in which the target motion for assessment is performed according to an example embodiment, and FIG. 11 is a diagram illustrating an example of assigning a score to an assessment factor of a target motion for assessment in a processor according to an example embodiment.

The processor may analyze motion information and a motion time of a human body to classify a target motion for assessment.

Referring to FIG. 9, at least one target motion for assessment may include a first assessment motion. The first assessment motion may be a motion of a first joint of the human body moving in a set direction from a first virtual line A-A' on the human body.

The processor may determine the first assessment motion based on a first assessment factor D and a second assessment factor E. The first assessment factor D and the second assessment factor E may each be an element having a set score. The first assessment factor D and the second assessment factor E may include conditions with respect to a single first assessment motion.

The processor may determine a score of the first assessment factor D and a score of the second assessment factor E based on whether the first assessment motion satisfies the respective conditions of the first assessment factor D and the second assessment factor E. When the first angle is at an angle within a first angle range from the first virtual line A-A', the processor may assign a score of 0 to each of the first assessment factor D and the second assessment factor E. When the first angle is at an angle within a second angle range from the first virtual line A-A', the processor may assign a score of 1 to the first assessment factor D and assign a score of 0 to the second assessment factor E. When the first angle is at an angle within a third angle range from the first virtual line A-A', the processor may assign a score of 1 to each of the first assessment factor D and the second assessment factor E.

The first angle range may be set to be about 0 to 30 degrees (°) from the first virtual line A-A'. The second angle range may be set to be about 30 to 60° from the first virtual line A-A'. The third angle range may be set to be about 60 to 90° from the first virtual line A-A'.

Referring to FIG. 10, in response to a human body performing a first assessment motion, a processor may sense a period of time in which the first assessment motion is performed. When the human body performs the first assessment motion, the processor may acquire a normal distribution of angle displacements of a first joint of the human body during a period of time in which the first assessment motion is performed. A motion time of the human body may be classified into an initiation phase, a motion phase, and a completion phase. Also, an onset phase for analyzing motion information of the human body may be set.

The processor may extract a standard deviation a of the first joint of the human body on a time-by-time basis from the normal distribution of the angle displacements of the first joint. The processor may extract standard deviations of angle displacements of the first joint in a window in a set size during the period of time in which the first assessment motion is performed, and acquire a graph of the standard deviation a of the angle displacements of the first joint acquired on the time-by-time basis. Here, the size of the window may be set as 0.2 seconds (s). The processor may determine a result value by multiplying a maximum standard deviation σmax among the extracted standard deviations σ by a set proportion value of, for example, about 5 percent (%). Also, the processor may set, to be a motion phase, a period of time $t_{max}-t_{min}$ from a point in time $t_{min}$ of a minimum value to a point in time $t_{max}$ of a maximum value among point in times $t_{id}$ corresponding to standard deviations having the same result value among the extracted standard deviations σ.

Also, in the normal distribution of the angle displacements of the first joint, the processor may set a period of time from a time-sensed point in time 0 to the point in time $t_{min}$ to be an initiation phase and set a period of time after the point in time $t_{min}$ to be a completion phase.

A confidence level of, for example, about 90% may be determined based on the set proportion value by which the maximum standard deviation σmax is multiplied among the standard deviations σ of the first joint acquired during the period of time in which the first assessment motion is performed. Also, remaining phases other than a portion verified as noise among the motion information may be used as information for analyzing in order to increase an accuracy of the analyzing. The processor may eliminate exercise information acquired in a period of time other than the motion phase.

The processor may set, to be an onset phase, a period of time $t_{min}-\alpha \sim t_{min}+\alpha$ from a point in time earlier than the point in time $t_{min}$ by a set amount of time α to a point in time later than the point in time $t_{min}$ by the amount of time α. For example, a period of time from a point in time earlier than the point in time $t_{min}$ by 0.5 seconds to a point in time later than the point in time $t_{min}$ by 0.5 seconds may be set to be the onset phase.

In the above scheme, the motion time of the human body may be classified into "on starting motion" and "during motion" to acquire motion information corresponding to a point in time required in an assessment tool such as an FMA. As such, by implementing the assessment tool as an actual algorithm, an assessment accuracy may be improved and an assessment may be automated.

Referring to FIG. 11, at least one target motion for assessment may include a second assessment motion. The second assessment motion may be a motion of a second joint of a human body moving in a set range from a second virtual line B-B' on the human body.

As described above, when the processor determines a time phase, the processor may determine the second assessment motion based on a third assessment factor. The third assessment factor may include a set condition with respect to the second assessment motion. The processor may determine a score of the third assessment factor based on whether the second assessment motion satisfies the third assessment factor.

The processor may extract a standard deviation of angle displacements of the second joint.

When the second joint is at an angle within a fourth angle range from the second virtual line B-B' based on the standard deviation of the angle displacements of the second joint, and when the standard deviation of the angle displacements of the second joint is less than a result value, the processor may assign a score of 1 to the third assessment factor. Here, the result value may be obtained similarly or identically to the result value determined in the example of FIG. 10.

When the second joint is at an angle within a fifth angle range from the second virtual line B-B' based on the standard deviation of the angle displacements of the second joint, or when the standard deviation of the angle displacements of the second joint is greater than or equal to the result value, the processor may assign a score of 0 to the third assessment factor.

Here, the fourth angle range may be set to be about 120 to 180° and the fifth angle range may be set to be about 0 to 120°.

The processor may classify whether a target motion for assessment required in an assessment tool satisfies an assessment condition as true or false, combine scores determined based on the first assessment factor, the second assessment factor, and the third assessment factor, and calculate a final assessment score of at least one target motion for assessment, thereby automating the assessment tool and increasing an assessment accuracy.

The at least one target motion for assessment may include a third assessment motion of the hand opening and closing as described with reference to FIG. 6.

The processor may determine the third assessment motion based on a fourth assessment factor. The fourth assessment factor may include a set condition with respect to the third assessment motion.

The processor may determine a score of the fourth assessment factor whether the third assessment motion satisfies the set condition of the fourth assessment factor. When the grasp force is not sensed or the grasp force is less than a set force, the processor may assign a score of 0 to the fourth assessment factor. When the grasp force is greater than or equal to the set force, the processor may assign a score of 1 to the fourth assessment factor. Here, the set force may be set as an average value of an average grasp force required by a user, for example, a physical therapist, for a human body using a pressure sensor.

FIG. 12 is a diagram illustrating an assessment condition for assigning a score to an assessment factor of a target motion of assessment in a processor according to an example embodiment and FIG. 13 is a diagram illustrating a table used for determining a final assessment score in a processor according to an example embodiment.

A processor may set a threshold value, a mean value, and a standard deviation (STD) value as set conditions of one or more target motion for assessment A, B, C, D, E, F, G, and H required in an assessment tool, for example, an FMA. The mean value and the STD value may be set based on experimental data including values sensed by a sensor. The processor may determine at least one assessment factor configuring at least one target motion for assessment to be a logical expression based on whether human body exercise information for analyzing the at least one target motion for assessment satisfies the threshold value, the mean value, and the STD value.

As described above, a final assessment score of the at least one target motion for assessment may be determined based on a combination of the at least one assessment factor. For example, the processor may determine the final assessment score using the following equation.

if $$A*B*C*E*F*G*H=1, FMA=2,$$

Else $$FAS=A*B*C*E*F'+A*B*C*E*F+A*B*C*D*F+ A*B*C*D*F'$$ [Equation]

In the above equation, A, B, and C denotes assessment factors of a second assessment motion in an initiation phase, D and E denote assessment factors of a first assessment motion in a motion phase, F, G, and H denote assessment factors of the second assessment motion in the motion phase, and FAS denotes a final assessment score.

With respect to a single target motion for assessment, assessment factors corresponding to the initiation phase and assessment factors corresponding to the motion phase may be present. The processor may determine a score of the at least one assessment factor based on the aforementioned scheme. The processor may determine whether "$A*B*C*E*F*G*H=1$" is satisfied, and then determine whether "$FMA=A*B*C*E*F'+A*B*C*E*F+A*B*C*D* F+A*B*C*D*F'$" is satisfied. For example, in response to a human body performing at least one target motion for assessment, a score of at least one assessment factor configuring the at least one target motion for assessment may be determined to be "(A, B, C, D, E, F, G, H)=(1, 1, 1, 1, 0, 1, 0, 0)". In this example, since $A*B*C*E*F*G*H$ is equal to 0, a final assessment score may be determined to be "$A*B*C*E*F'+A*B*C*E*F+A*B*C*D*F+A*B*C*D* F'=1*1*1*0*0+1*1*1*0*1+1*1*1*1*1+1*1*1*1*0=1$".

As the foregoing, the present disclosure is applicable to various examples. The foregoing description is merely an example of determining a final assessment score and is not to be taken as being limited thereto.

Figure 14:
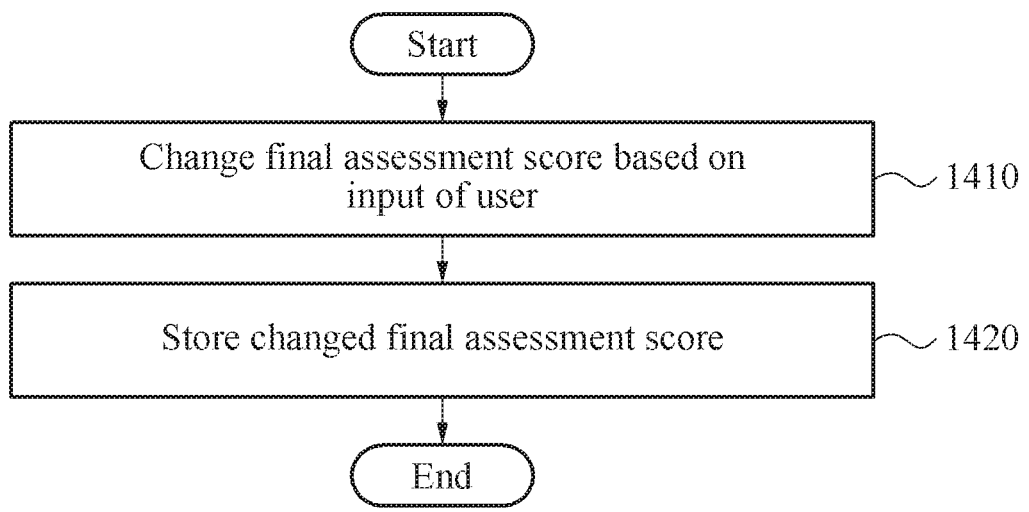
FIG. 14 is a flowchart illustrating an example of changing a final assessment score in a processor according to an example embodiment.

FIG. 14 is a flowchart illustrating an example of changing a final assessment score in a processor according to an example embodiment.

As discussed above, a processor may determine a final assessment score. When a user determines that the final assessment score is incorrect, the processor may correct the final assessment score.

Referring to FIG. 14, in operation 1410, the processor may change a final assessment score determined based on a user input to a final assessment score input by a user.

In operation 1420, the processor stores the changed final assessment score and exercise information of a human body. The stored final assessment score may be used for machine learning of the processor.

Figure 15:
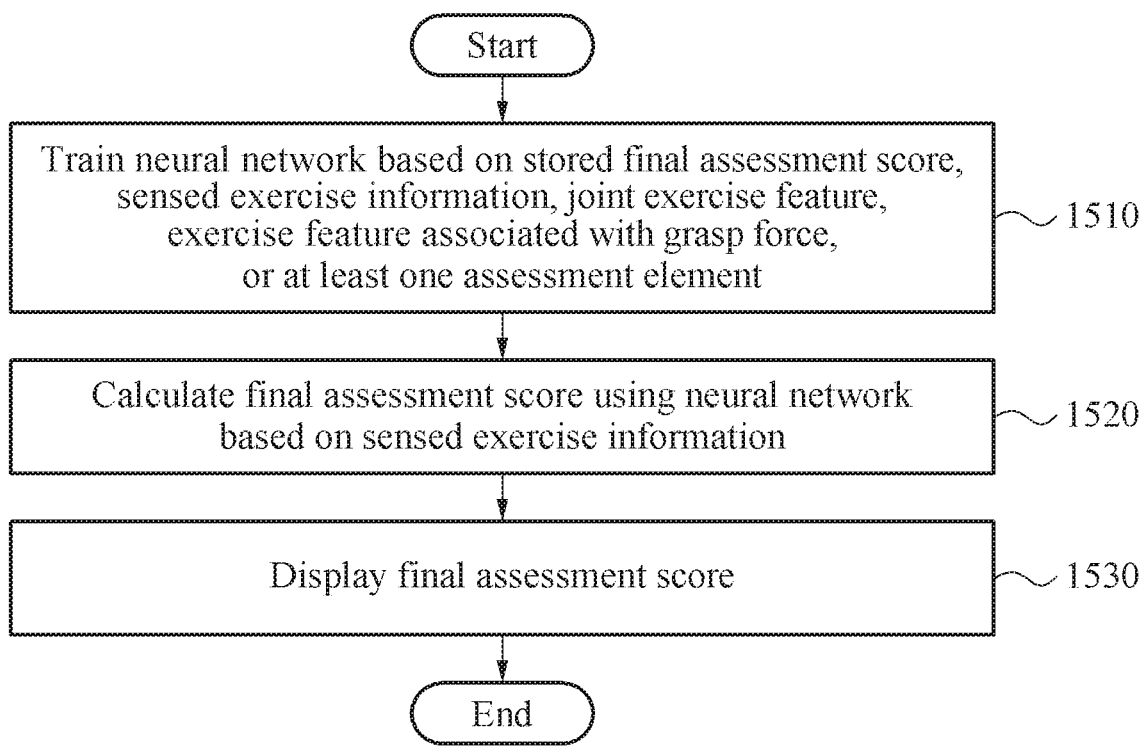
FIG. 15 is a flowchart illustrating an example of calculating an FMA score in a processor according to an example embodiment.

FIG. 15 is a flowchart illustrating an example of calculating an FMA score in a processor according to an example embodiment.

A processor may calculate a final assessment score and store the final assessment score and exercise information of a human body as described above. Through this, the final assessment score and the exercise information may be used to train a neural network included in the processor. When new data is input to the processor, the processor may automatically calculate a final assessment score.

Referring to FIG. 15, in operation 1510, the processor may train a neural network based on a stored final assessment score, sensed exercise information, a joint exercise feature, an exercise feature associated with a grasp force, or at least one assessment factor. For example, a support vector machine (SVM) may be used to train the neural network.

In operation 1520, the processor may automatically calculate a final assessment score using the neural network based on newly sensed exercise information.

In operation 1530, the processor displays the calculated final assessment score.

According to an aspect, it is possible to provide a motor function assessment system that calculates a final assessment score of a target motion for assessment with increased accuracy and confidence level by objectifying an FMA which have been conducted subjectively by a clinician in general.

According to another aspect, it is possible to provide a motor function assessment system that automatically calculates a final assessment score of a target motion for assessment based on human body motion information newly input through machine learning by accumulating result data including the final assessment score of the target motion for assessment.

According to still another aspect, it is possible to provide a motor function assessment system that uses a contactless sensor which is also applicable to a user with a brain disease.

According to yet another aspect, it is possible to provide a motor function assessment system that minimizes a number of sensors configured to sense human body exercise information.

According to a further aspect, it is possible to provide a motor function assessment system that determines a final assessment score of a target motion for assessment independently of a large amount of patient experiment data and accurately assessed patient data.

Effects of a motor function assessment system are not limited to those mentioned above, and other effects can be clearly understood to those skilled in the art from the above description.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A system for assessing a motor function of a human body, the system operating to provide a final assessment score calculated using scoring of assessment motions of human body joints and statistical information acquired on joint displacement, to achieve an increased accuracy and increased confidence level of the system, allowing a reduced use of sensors, the system comprising:

a processor configured to determine the final assessment score of a target motion for assessment based on human body exercise information, obtained from at least one sensor, wherein the at least one sensor includes a motion recognition sensor, including a joint position and a joint orientation in the human body, wherein the target motion for assessment includes:
 a first assessment motion of a first joint of the human body moving in a set direction from a first virtual line of the human body; and
 a second assessment motion of a second joint of the human body moving in a set range from a second virtual line of the human body, and wherein the processor is further configured to:
 determine an assessment score of the first assessment motion by a first assessment factor and a second assessment factor;
 assign a score of 0 to each of the first assessment factor and the second assessment factor when the first joint is at an angle within a first angle range from the first virtual line;
 assign a score of 1 to the first assessment factor and a score of 0 to the second assessment factor when the first joint is at an angle within a second angle range from the first virtual line;
 assign a score of 1 to each of the first assessment factor and the second. assessment factor when the first joint is at an angle within a third angle range from the first virtual line;
 identify a period of time in which the first assessment motion is performed;
 acquire a normal distribution of angular displacements of the first joint in said identified period of time;
 extract from said acquired normal distribution standard deviations of angular displacements of the first joint in a window of a set size on a time-by-time basis;
 determine a result value obtained by multiplying, by a set proportion value, a maximum standard deviation having a greatest value among the extracted standard deviations;
 set, to be a motion phase, a period of time from a point in time of a minimum. value, among points in time corresponding to standard deviations of which the result value is the same among the extracted standard deviations to a point in time of a maximum value among the points in time; and
 determine the final assessment score of the target motion for assessment based on a set condition using said first assessment factor and said second assessment factor of the first assessment motion, an assessment factor of the second assessment motion and said result value.

2. The system of claim 1, wherein the processor is further configured to:
 determine an assessment score of the second assessment motion by a third assessment factor;
 extract a standard deviation of angular displacements of the second joint;
 assign a score of 1 to the third assessment factor when the second joint is at an angle within a fourth angle range from the second virtual line and the standard deviation of the angular displacements of the second joint is less than. the result value; and
 assign a score of 0 to the third assessment factor when the second joint is at an angle within a fifth angle range from the second virtual line or the standard deviation of the angular displacements of the second joint is greater than equal to the standard deviation of the angular displacements of the first joint.

3. The system of claim 1, wherein the processor is further configured to set, to be an onset phase, a period of time from a point in time earlier than the point in time of the minimum value by a set amount of time to a point in time later than the point in time of the minimum value by the amount of time.

4. The system of claim 1, wherein the processor is further configured to discard human body exercise information acquired in a period of time other than the motion phase.

5. The system of claim 1, wherein the human body exercise information includes a grasp force of the human body and the target motion for assessment includes a third assessment motion of a hand of the human body opening and closing, and
wherein the processor is further configured to:
determine an assessment score of the third assessment motion based on a fourth assessment factor;
assign a score of 0 to the fourth assessment factor when the grasp force is not sensed or the grasp force is less than a set force; and
assign a score of 1 to the fourth assessment factor when the grasp force is greater than or equal to the set force.

6. The system of claim 1, wherein the processor is further configured to determine the final assessment score using an equation as follows:

if $$A*B*C*E*F*G*H=1, FAS=2,$$

Else $$FAS=A*B*C*E*F'+A*B*C*E*F+A*B*C*E*F+ \\ A*B*C*D*F+A*B*C*D*F',$$

where A, B, and C denote assessment factors of the second assessment motion in an onset phase, D and F denote assessment factors of the first assessment motion in a motion phase, F, G, and H denote assessment factors of the second assessment motion in the motion phase, F' denotes an inverse value of F in Boolean Algebra and FAS denotes the final assessment score.

* * * * *